(12) United States Patent
Stokes et al.

(10) Patent No.: US 9,427,430 B2
(45) Date of Patent: Aug. 30, 2016

(54) COMPRESSION BANDAGE HAVING AN INTEGRATED STRAIN GAUGE

(71) Applicant: KCI Licensing, Inc., San Antonio, TX (US)

(72) Inventors: Benjamin Stokes, Ringwood (GB); Timothy Mark Robinson, Basingstoke (GB)

(73) Assignee: KCI Licensing, Inc., San Antonio, TX (US)

( * ) Notice: Subject to any disclaimer, the term of this patent is extended or adjusted under 35 U.S.C. 154(b) by 316 days.

(21) Appl. No.: 14/206,573

(22) Filed: Mar. 12, 2014

(65) Prior Publication Data

US 2014/0276275 A1    Sep. 18, 2014

Related U.S. Application Data

(60) Provisional application No. 61/784,861, filed on Mar. 14, 2013.

(51) Int. Cl.
| | |
|---|---|
| *A61L 15/00* | (2006.01) |
| *A61K 31/427* | (2006.01) |
| *A61H 1/00* | (2006.01) |
| *A61F 13/00* | (2006.01) |
| *A61K 9/00* | (2006.01) |
| *A61K 47/40* | (2006.01) |

(52) U.S. Cl.
CPC ....... *A61K 31/427* (2013.01); *A61F 13/00038* (2013.01); *A61F 13/00059* (2013.01); *A61H 1/008* (2013.01); *A61K 9/0048* (2013.01); *A61K 47/40* (2013.01); *A61F 2013/00123* (2013.01); *Y10T 29/49826* (2015.01); *Y10T 156/10* (2015.01)

(58) Field of Classification Search
CPC .............. A61F 13/00038; A61F 13/00059; A61F 2013/00123; A61F 9/0017; A61F 9/04; A61F 13/00; A61F 2013/00957; A61F 13/064; A61F 2013/00119; A61F 2013/00153; A61F 2013/8497; A61F 5/01; A61H 1/008; A61K 31/427; A61K 47/40; A61K 9/0048; Y10T 156/10; Y10T 29/49826
USPC .............................. 602/41, 56, 75
See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |

(Continued)

FOREIGN PATENT DOCUMENTS

| | | |
|---|---|---|
| AU | 550575 A1 | 3/1986 |
| AU | 745271 | 4/1999 |

(Continued)

OTHER PUBLICATIONS

International Search Report and Written Opinion for corresponding PCT/US2014/024894 mailed Jun. 3, 2014.

(Continued)

*Primary Examiner* — Michael Brown

(57) ABSTRACT

A compression therapy apparatus and a method for manufacturing and applying compression with the same may include a bandage and a tension indicator coupled to the bandage. A tension indicator may include a film having layers of liquid crystal droplets deposited on a polymer matrix. The tension indicator can be adapted to color shift under tension between the first end and the second end of the bandage.

40 Claims, 5 Drawing Sheets

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,613,679 A | 10/1971 | Bijou | |
| 3,648,692 A | 3/1972 | Wheeler | |
| 3,682,180 A | 8/1972 | McFarlane | |
| 3,826,254 A | 7/1974 | Mellor | |
| 3,872,050 A * | 3/1975 | Benton | C09K 19/544 349/20 |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 5,778,236 A | 7/1998 | Gephardt et al. | |
| 6,050,967 A * | 4/2000 | Walker | A61F 13/00059 602/75 |
| 6,071,267 A | 6/2000 | Zamierowski | |
| 6,135,116 A | 10/2000 | Vogel et al. | |
| 6,142,968 A | 11/2000 | Pigg et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,432,074 B1 | 8/2002 | Ager et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 8,827,973 B2 | 9/2014 | Stokes et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2006/0079852 A1 | 4/2006 | Bubb et al. | |
| 2011/0232560 A1* | 9/2011 | King | B65H 35/0026 116/201 |
| 2013/0131565 A1* | 5/2013 | Dallafior | A61F 5/01 602/5 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 4/2002 |
| WO | 80/02182 | 10/1980 |
| WO | 87/04626 | 8/1987 |
| WO | 90/10424 | 9/1990 |
| WO | 93/09727 | 5/1993 |
| WO | 94/20041 | 9/1994 |
| WO | 96/05873 | 2/1996 |
| WO | 97/18007 | 5/1997 |
| WO | 99/13793 | 3/1999 |
| WO | 01/92843 A2 | 12/2001 |

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (certified translation).

(56) References Cited

OTHER PUBLICATIONS

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Ðukić, Ž. Maksimović, Ð. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).

\* cited by examiner

COMPRESSION BANDAGE HAVING AN INTEGRATED STRAIN GAUGE

Under 35 U.S.C. §119(e), this application claims priority to and the benefit of U.S. Provisional Patent Application No. 61/784,861 filed Mar. 14, 2013, entitled "Compression Bandage having an Integrated Strain Gauge," the disclosure of which is hereby incorporated by reference in its entirety.

TECHNICAL FIELD

The present disclosure relates generally to compression therapy and, more particularly, but not by way of limitation, to compression therapy apparatuses and systems having an integrated strain gauge, and methods for making and using the same.

BACKGROUND

Many people suffer from venous disease, which are conditions related to veins that become diseased or abnormal. For example, vein walls may become weak or damaged, causing the blood to flow backward when muscles surrounding the veins relax. Backwards flow of blood may cause high pressure in the veins, resulting in stretching, twisting, and swelling of veins. Venous disease may include spider veins, varicose veins, leg swelling and leg pain, chronic venous insufficiency, leg epidermis changes, leg ulcers, phlebitis, vascular malformations, and venous malformations, for example. Mild venous disease does not typically affect the day to day life of a person suffering from venous disease; however, severe cases can be debilitating.

To facilitate healing of venous disease, a firm-fitting wrap or elastic bandage may be used to apply compression to a limb or other tissue site. The bandage must be held in tension as it is applied to the limb or other tissue site. However, it may be difficult to determine whether an appropriate amount of tension is being applied to the bandage during its application, potentially decreasing the effectiveness of the compression therapy.

SUMMARY

According to some illustrative embodiments, a compression therapy apparatus is described. The compression therapy apparatus may include a bandage having a first end, a second end, and a length extending between the first end and the second end. The compression therapy apparatus may also include a tension indicator. The tension indicator may include a film having layers of liquid crystal droplets deposited on a polymer matrix. The tension indicator may be coupled to the bandage and may be adapted to color shift under tension between the first end and the second end.

According to other illustrative embodiments, a method of manufacturing a bandage is described. A bandage having a first end, a second end, and a length extending between the first end and the second end may be provided. A tension indicator may be coupled to the bandage. The tension indicator may be adapted to color shift under tension between the first end and the second end of the bandage. The tension indicator may include a film having layers of liquid crystal droplets deposited on a polymer matrix.

According to other illustrative embodiments, a method for providing compression therapy to a tissue site is described. A compression therapy apparatus may be provided. The compression therapy apparatus may include a bandage having a first end, a second end, and a length extending between the first end and the second end. The compression therapy apparatus may also include a tension indicator. The tension indicator may include a film having layers of liquid crystal droplets deposited on a polymer matrix. The tension indicator may be coupled to the bandage and may be adapted to color shift under tension between the first end and the second end. The first end of the bandage may be secured to the tissue site and tension may be applied to the bandage. The tension indicator may be monitored for the color shift. If the tension indicator color shifts, the bandage may be wrapped around the tissue site.

Other aspects, features, and advantages of the illustrative embodiments may become apparent with reference to the drawings and detailed description that follow.

DETAILED DESCRIPTION OF ILLUSTRATIVE EMBODIMENTS

New and useful systems, methods, and apparatuses for providing compression therapy to a tissue site are set forth in the appended claims. Objectives, advantages, and a preferred mode of making and using the systems, methods, and apparatuses may be understood best by reference to the following detailed description in conjunction with the accompanying drawings. The description provides information that enables a person skilled in the art to make and use the claimed subject matter, but may omit certain details already well-known in the art. Moreover, descriptions of various alternatives using terms such as "or" do not necessarily require mutual exclusivity unless clearly required by the context. The claimed subject matter may also encompass alternative embodiments, variations, and equivalents not specifically described in detail. The following detailed description should therefore be taken as illustrative and not limiting.

The example embodiments are generally described herein in the context of compression therapy applications. Spatial relationships between various elements or to the spatial orientation of various elements may be described as depicted in the attached drawings. In general, such relationships or orientations assume a frame of reference consistent with or relative to a patient in a position to receive compression therapy. However, as should be recognized by those skilled in the art, this frame of reference is merely a descriptive expedient rather than a strict prescription.

Figure 1:
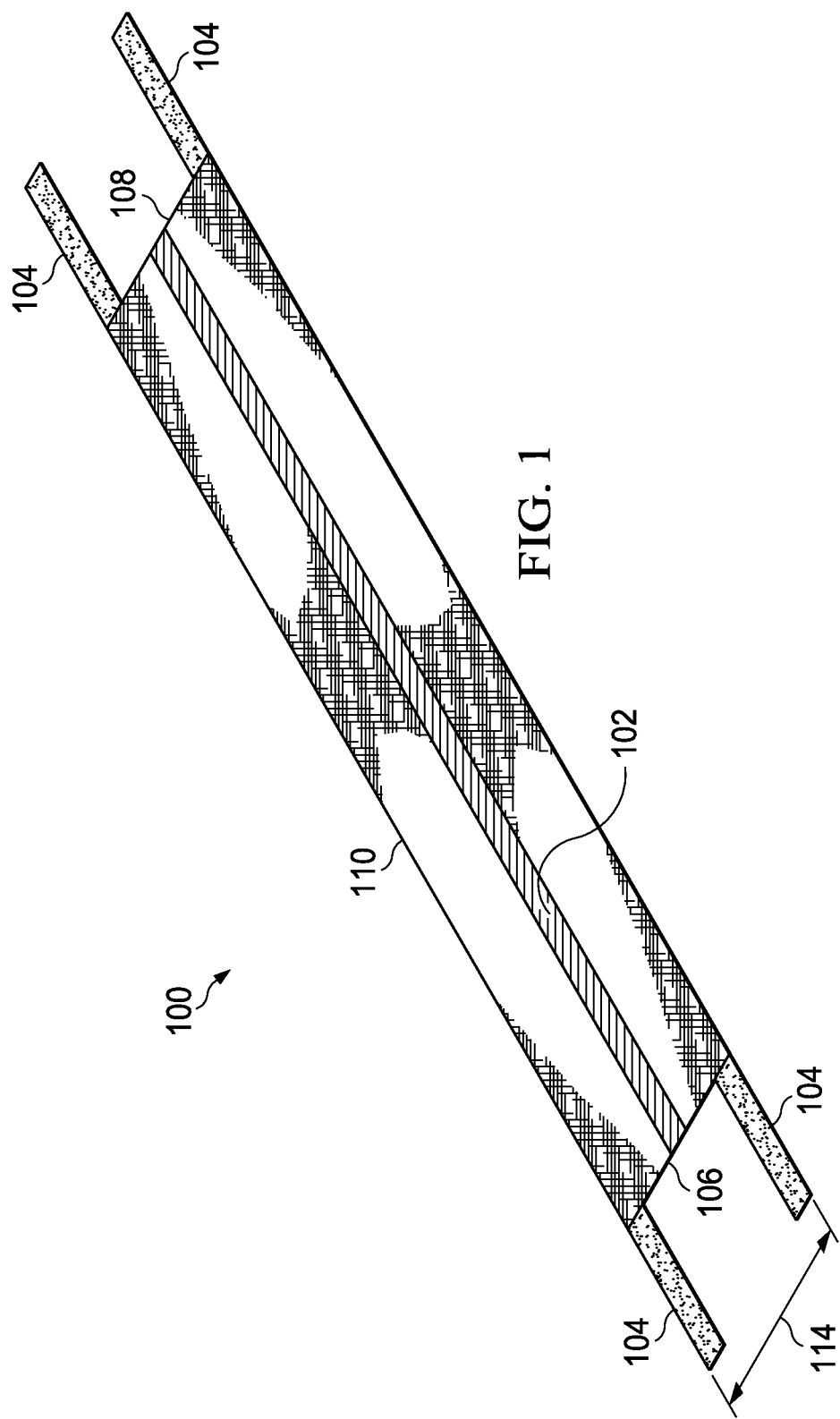
FIG. 1 is a perspective view of a bandage in accordance with an exemplary embodiment.

FIG. 1 is a perspective view, illustrating details that may be associated with some embodiments of a compression therapy apparatus 100 that can provide therapeutic compression of a tissue site in accordance with this specification. As illustrated, the compression therapy apparatus 100 may have a bandage, such as a bandage 110, one or more tension indicating members, such as tension indicator 102, and one or more attachment devices, such as couplers 104. The bandage 110 may have a first end 106, a second end 108, a length, and a width 114. In some embodiments, a first end, a second end, a length, and a width of the compression therapy apparatus 100 may coincide with the first end 106, the second end 108, the length, and the width 114 of the bandage 110. In some embodiments, the compression therapy apparatus 100 may be adapted to receive a limb, such as a portion of a leg.

Figure 2:
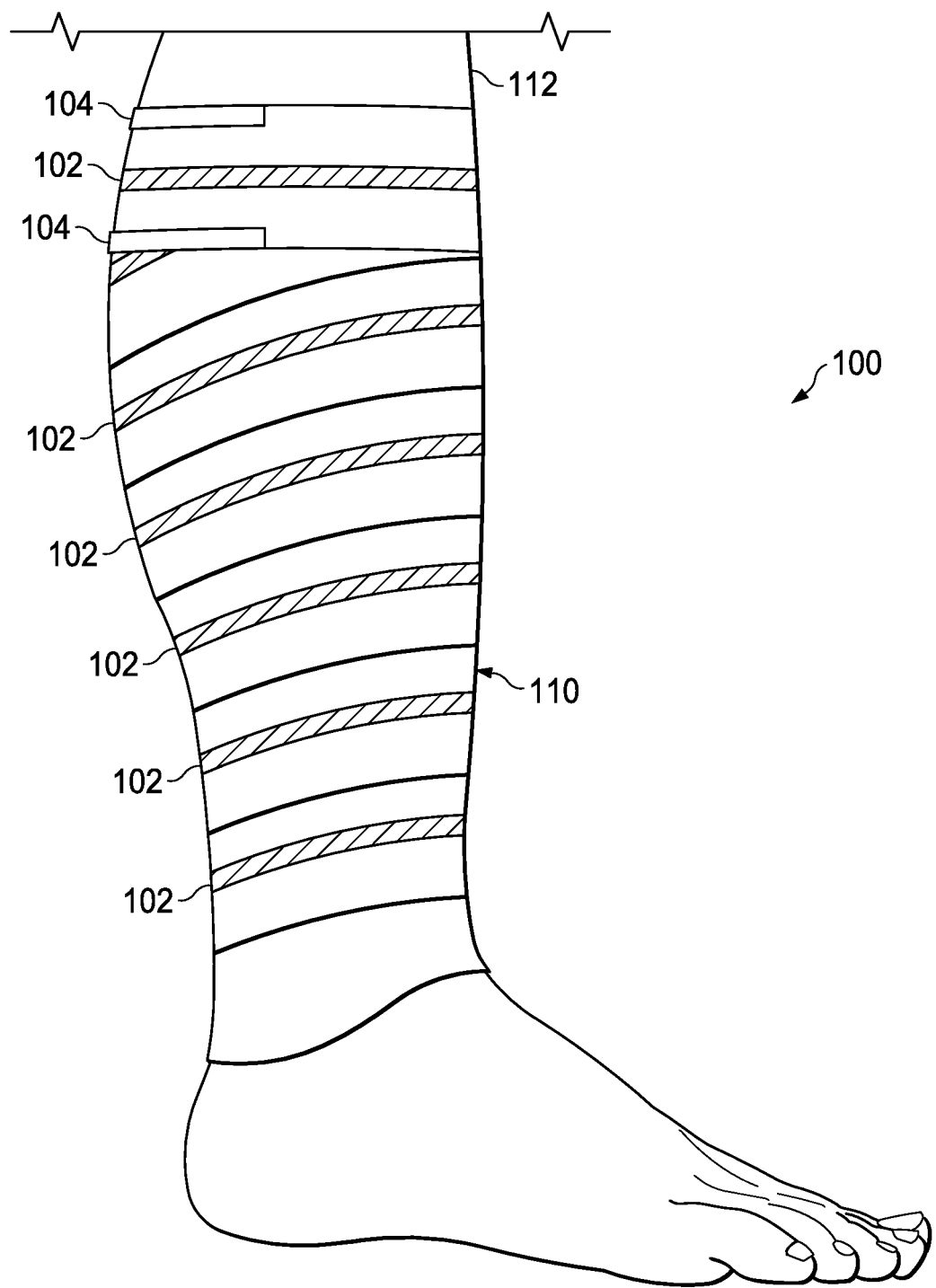
FIG. 2 illustrates the bandage of FIG. 1 applied to a tissue site.

FIG. 2 is an elevation view, illustrating additional details that may be associated with some embodiments of the compression therapy apparatus 100. The compression therapy apparatus 100 may be adapted to cover a limb, such as a portion of a leg 112. For example, the leg 112 may be wrapped with the bandage 110. The bandage 110 may generally represent any type of bandage, stocking, wrap, or other garment suitable for contact with a tissue site. Generally, the bandage 110 may be formed of an elastic material that may be adapted to create significant pressure on a tissue site. In some embodiments, the bandage 110 may be formed of a combination of latex, rubber, cotton, polyester, or latex-free elastic yarns. The bandage 110 may be formed of other materials that may be comfortable in contact with a tissue site or epidermis surrounding a tissue site. In other exemplary embodiments, the compression therapy apparatus 100 may be provided in multiple sizes to fit varying leg sizes. For example, the length of bandage 110 may be varied so that the compression therapy apparatus 100 may be adapted to fit smaller or larger limbs. Additionally or alternatively, the width 114 may be adapted to fit smaller or larger limbs.

The couplers 104 may be suitable devices configured to secure the compression therapy apparatus 100 to a limb, such as the leg 112. In some embodiments, the compression therapy apparatus 100 may be applied to the leg 112 by placing the first end 106 proximate to an ankle of the leg 112. The compression therapy apparatus 100 may then be wrapped around the ankle so that a portion of the compression therapy apparatus 100 may overlap at least a portion of the first end 106. The couplers 104 may have a first end that secures to a portion of the first end 106 of the bandage 110, and a second end that secures to a portion of the bandage 110 overlapping the first end 106. Securing opposing ends of the couplers 104 to different portions of the bandage 110 may secure the compression therapy apparatus 100 to the ankle of the leg 112. In some embodiments, the couplers 104 may be devices configured to adhere to the bandage 110, such as tape, for example. In other embodiments, the couplers 104 may be aluminum or plastic devices having a member configured to at least partially pierce the bandage 110 to secure the coupler 104. In still other exemplary embodiments, the coupler 104 may be a hook-and-loop device. The couplers 104 may have sufficient strength to maintain a tension applied to the bandage 110 as described in more detail below.

The compression therapy apparatus 100 may be particularly beneficial for treating venous disease, such as leg ulcers and oedema, which are often treated with compression therapy. As the pressure within the veins of a standing subject may largely be hydrostatic, the external pressure which may be necessary to counteract effects of venous disease may decrease progressively up a limb, especially a leg. A decreasing amount of compression may be needed as the hydrostatic head within a limb is effectively reduced. For this reason, external compression may be applied in a graduated fashion, with the highest pressure at a distal end of a limb, such as an ankle of a leg. Compression of a limb may increase pressure within veins of the limb and, particularly veins proximate to a surface of the limb. Veins proximate to a surface of a limb may also be known as superficial veins. Compression may generally encourage blood flow from superficial veins toward deeper veins where blood may be more readily carried out of a limb. Increased pressure in veins can decrease swelling and reduce symptoms of venous disease.

Compression therapy can be difficult to apply and may require different compression on different portions of a limb. Variation of compression on a limb or other tissue site to encourage blood flow in a desired direction may generally be referred to herein as a "compression profile." For example, a compression profile may be prescribed to encourage blood flow from an ankle to a thigh of a leg. As described above, compression may usually be graduated with the highest pressure at the ankle and the lowest pressure at higher parts of a leg proximate to a knee or pelvis.

The current British Standard for compression hosiery (BS 6612:1985) describes three different classes of stockings. The three different classes may provide compression at an ankle ranging from about 14 mmHg to about 35 mmHg. Pressure developed beneath a bandage may be governed by the tension in the bandage, the radius of curvature of a limb, and the number of layers of a bandage applied to a limb. Applying a bandage with a 50% overlap, that is applying the bandage so that at least 50% of the width of each layer of the bandage overlaps the previous layer, may produce two layers of bandage and may generate a sub-bandage pressure twice the sub-bandage pressure produced by applying a bandage with 0% overlap. Sub-bandage pressure may be a pressure at a surface of a limb beneath a bandage. Sub-bandage pressure may be calculated using a formula derived from the Laplace equation. The sub-bandage pressure equation is as follows:

$$P = (TN \times 4630)/CW$$

In the sub-bandage pressure equation, P is the pressure in mmHg, T is the bandage tension in kgf, C is the circumference of the limb in cm, W is the bandage width in cm, and N is the number of layers applied. According to this equation, sub-bandage pressure is directly proportional to bandage tension and inversely proportional to a radius of curvature of a limb to which a bandage is applied. A bandage applied with constant tension to a limb of normal proportions, that is a limb with a circumference that increases from a distal end of the limb to a proximal end of the limb, may produce a graduated compression profile with the highest sub-bandage pressure located proximate to the distal portion of the limb. For example, the leg 112 may have an approximated diameter that increases as the leg 112 transitions from the ankle portion to the knee portion. If the compression therapy apparatus 100 is applied with constant tension to the leg 112, the graduated compression profile may be produced. The graduated compression profile may have the highest sub-bandage pressure proximate to the ankle and the lowest proximate to the knee.

Successful application of a prescribed compression profile to a limb or other tissue site with a conventional compression bandage may be highly dependent on the experience of the treating clinician. Clinicians may often find it difficult to maintain the appropriate tension on the compression bandage while wrapping the bandage around a limb to achieve a desired compression profile. If the bandage is applied too loosely, the bandage may be ineffective. If the bandage is applied too tightly, the bandage may cause tissue damage and necrosis. In extreme cases, applying the bandage too tightly may lead to amputation, particularly where arterial disease is present in a limb. The time required for a clinician to properly apply compression therapy may be significant and may be a major element of the total cost of treating venous disease, such as venous leg ulcers. The successful management of venous leg disease represents a significant clinical problem and a major drain on limited financial resources. In 1991, the annual costs to the National Health Service of the United Kingdom due to leg ulceration issues were estimated to be as high as £230 to £400 million.

Existing bandages may include devices to aid in determining whether the appropriate tension is being applied to the bandage for a desired compression profile. Generally, these devices may depend on a person applying the bandage to subjectively identify whether the bandage is appropriately tensioned during application of the bandage to the limb. Some bandages have incorporated an icon or shape that may be either printed or sewn onto the bandage. The icon or shape may act as an indicator to determine whether the correct tension is applied to the bandage during application. As the bandage is elastically deformed or stretched, the shape stretches in response. The appropriate tension is applied to the bandage if the deformed shape matches a predetermined geometric pattern. The icon or shape must be closely monitored and judged to determine if the icon matches the geometric pattern. Correctly identifying a change in a geometric shape may be difficult to do. For example, as the bandage is wrapped around the limb, distortion of the shape caused by the curvature of the limb may lead to an incorrect determination that the desired tension is being applied to the bandage. As a result, the bandage may not apply a desired compression. Similarly, a slightly changed shape may be interpreted to indicate that the proper tension is applied when not enough tension is applied. Still further, a determination that the shape has not fully changed may cause too much tension to be applied. In each case, treatment of the venous disease may be unsuccessful due to the misjudgment of the icon or shape during application of tension to the bandage.

As disclosed herein, the compression therapy apparatus 100 can overcome these shortcomings and others by providing a bandage having tension indicators that may provide a visual cue to a clinician that an appropriate amount of tension has been applied without requiring the clinician to subjectively interpret the visual cue.

Figure 3:
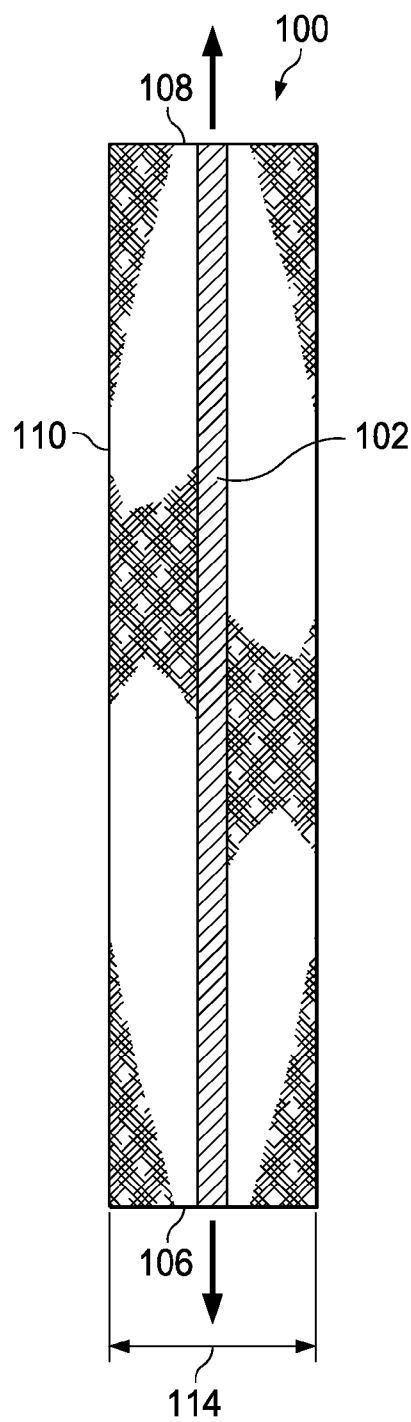
FIG. 3 is a plan view of the bandage of FIG. 1.

FIG. 3 is a plan view, illustrating additional details that may be associated with some embodiments of the compression therapy apparatus 100. The tension indicator 102 may be disposed proximate to a middle portion of the width 114 of the bandage 110. In some embodiments, the tension indicator 102 may be co-extensive with the length of the bandage 110 and may have a width less than the width 114 of the bandage 110. The tension indicator 102 may be coupled to the bandage 110 and may be configured to elastically deform at substantially the same rate as the elastic deformation of the bandage 110. If the tension indicator 102 and the bandage 110 elastically deform at substantially the same rate, the elastic deformation experienced by the bandage 110 may be experienced by the tension indicator 102.

In some embodiments, the tension indicator 102 may be a holographically formed polymer dispersed liquid crystal (H-PDLC) film. An H-PDLC film may include layers of liquid crystal droplets disposed in a polymer matrix. The liquid crystal droplets may be placed in the polymer matrix and polymerized by a holographic light to reflect light at a particular wave-length. After formation, if the polymer matrix is deformed, for example, by stretching the polymer matrix, the refractive index of the liquid crystal droplets may change so that the liquid crystal droplets reflect light at a different wave-length, causing the H-PDLC film to appear to change color or color shift. The positioning of the liquid crystal droplets may be controlled during the formation of the H-PDLC film so that the liquid crystal droplets may reflect a certain wave-length of light at a particular amount of deformation, allowing the H-PDLC film to act as a reflective strain gauge. For example, if the H-PDLC film forming the tension indicator 102 is subjected to a predetermined level of tension, the H-PDLC film, and consequently the tension indicator 102, may change from a clear or milky state to a blue state. The clear or milky state may generally refer to a color state of the tension indicator 102 where the tension indicator 102 lacks color. In the clear or milky state, the tension indicator 102 may be transparent, opaque, or have a translucence between transparent and opaque. In other exemplary embodiments, the H-PDLC film forming the tension indicator 102 may be subjected to a compressive force, causing the tension indicator 102 to change from a clear or milky state to a red state. In either tension or compression, when the tension indicator 102 changes color, i.e. from clear to blue or from clear to red, the tension indicator 102 may be referred to as undergoing or experiencing a color shift or color shifting.

The H-PDLC film can be manufactured to color shift as desired. For example, the H-PDLC film may be manufactured to color shift if the H-PDLC film is subjected to a particular tension. Similarly, the H-PDLC film may be manufactured to color shift if the H-PDLC film is subjected to a tension other than a desired tension. A desired amount of tension may correspond with a particular amount of strain in the bandage 110 and the tension indicator 102. In some embodiments, the tension indicator 102 may be selected for the compression therapy apparatus 100 so that the tension indicator 102 may color shift at the selected amount of strain. Consequently, if the correct tension is applied to the compression therapy apparatus 100, the tension indicator 102 may experience the selected strain and color shift. In some embodiments, the tension indicator 102 may experience a color shift from clear to blue when a pre-determined amount of tension is applied to the compression therapy apparatus 100. The pre-determined amount of tension may cause a known strain of the bandage 110 and the tension indicator 102, causing the tension indicator 102 to color shift if the appropriate tension is applied to the compression therapy apparatus 100.

In some embodiments, a single tension indicator 102 may be coupled to the bandage 110. The tension indicator 102 may be positioned proximate to a middle portion of the width 114 of the bandage 110 and may extend the length of the bandage 110. In some embodiments, if a pre-determined amount of tension is applied to the compression therapy apparatus 100 as indicated by the arrows of FIG. 3, the tension indicator 102 may color shift from clear to blue. In some embodiments, the tension indicator 102 may be secured to the bandage 110 during the manufacturing process of the compression therapy apparatus 100, for example, by weaving the tension indicator 102 into the bandage 110. In other embodiments, the tension indicator 102 may be secured to the bandage 110 after manufacturing the compression therapy apparatus 100, for example, by bonding, sewing, or otherwise securing the tension indicator 102 to a surface of the bandage 110.

As shown in FIG. 2, the compression therapy apparatus 100 may be wrapped around the leg 112. To wrap the leg 112, the first end 106 of the compression therapy apparatus 100 may be positioned proximate to the ankle of the leg 112, and the compression therapy apparatus 100 may be wrapped around the ankle so that at least a portion of the compression therapy apparatus 100 overlaps the first end 106 of the compression therapy apparatus 100. In some embodiments, at least two couplers 104 may be used to secure the portion of the compression therapy apparatus 100 overlapping the first end 106 of the compression therapy apparatus 100 to the first end 106 of the compression therapy apparatus 100. The couplers 104 may prevent the compression therapy apparatus 100 from unraveling during the application of the remaining portions of the compression therapy apparatus 100. The second end 108 of the compression therapy apparatus 100 may be pulled to apply a tension to the compression therapy apparatus 100. A color shift of the tension indicator 102 may indicate a desired tension. While holding the compression therapy apparatus 100 in tension and monitoring the tension indicator 102 to ensure that the tension indicator 102 maintains the color shift, the compression therapy apparatus 100 may be wrapped around the leg 112. Once the compression therapy apparatus 100 has been wrapped around the leg 112, the second end 108 of the compression therapy apparatus 100 may be proximate to the knee of the leg 112. The couplers 104 may be used to secure the second end 108 to an adjacent portion of the compression therapy apparatus 100, thereby maintaining the tension on the compression therapy apparatus 100 for application of compression therapy.

In some embodiments, the tension indicator 102 may provide an indication of the amount of overlap of the bandage 110 during the wrapping process. For example, if the tension indicator 102 is disposed near a center portion of the width 114 of the bandage 110, the compression therapy apparatus 100 may be wrapped so that a lower edge of a subsequent layer may placed proximate to an edge of the tension indicator 102 without overlapping the tension indicator 102. In this manner, the upper portion of a prior layer may be covered by a lower portion of a subsequent layer without obstructing the view of the tension indicator 102. In some embodiments, wrapping the compression therapy apparatus 100 in this manner may aid in maintaining a 50% overlap of the compression therapy apparatus 100, where a 50% overlap is prescribed.

Figure 4:
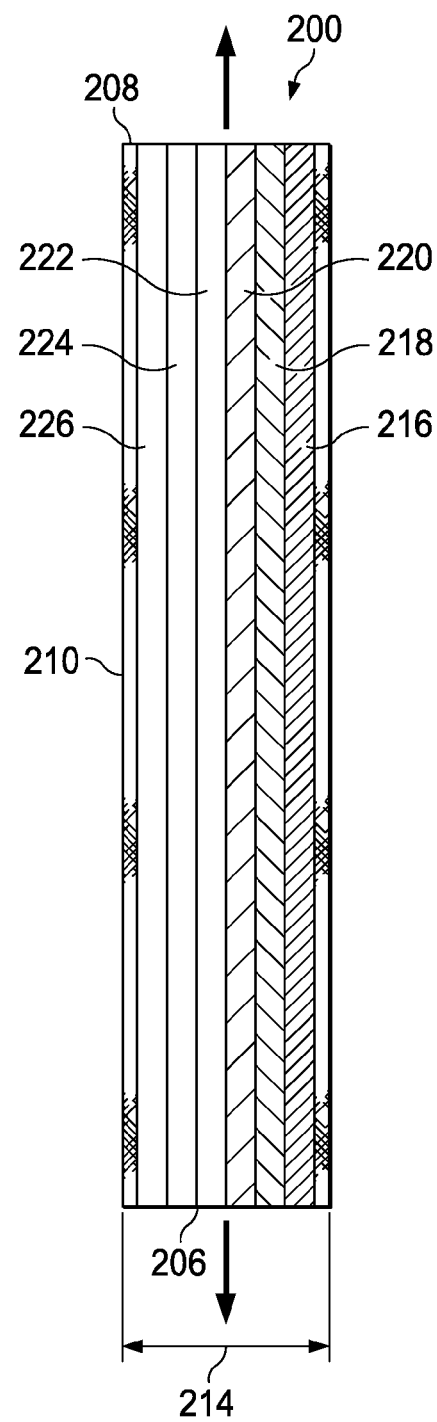
FIG. 4 is a plan view of another bandage in accordance with another embodiment.
Figure 5:
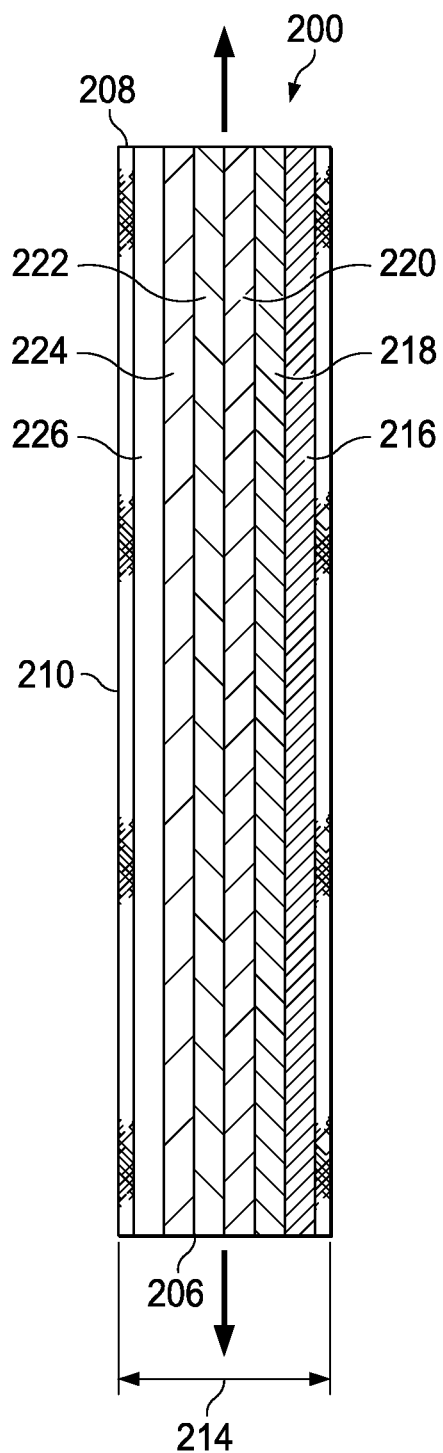
FIG. 5 is a plan view of the bandage of FIG. 4.

FIG. 4 and FIG. 5 are plan views, illustrating additional details that may be associated with another example embodiment of a compression therapy apparatus 200. The compression therapy apparatus 200 may be similar to and may include the components of the compression therapy apparatus 100, modified as described in more detail below. Similar elements may include similar reference numbers indexed by 100. The compression therapy apparatus 200 may include a bandage 210 and tension indicators 216, 218, 220, 222, 224, and 226. Each tension indicator 216, 218, 220, 222, 224, and 226 may be similar to and operate in a manner similar to the tension indicator 102 described above.

The tension indicators 216, 218, 220, 222, 224, and 226 may be disposed on the bandage 210 so that the tension indicators 216, 218, 220, 222, 224, and 226 are distributed across the width 214 of the bandage 210 in some embodiments. As shown in FIG. 4 and FIG. 5, for example, the tension indicators 216, 218, 220, 222, 224, and 226 may be apportioned across the width 214. In more particular embodiments, the tension indicators 216, 218, 220, 222, 224, and 226 may be apportioned equally, so that the width of each of the tension indicators 216, 218, 220, 222, 224, and 226 is substantially equal. In some embodiments, the tension indicators 216, 218, 220, 222, 224, and 226 may also be disposed in parallel on the bandage 210. Any or all of the tension indicators 216, 218, 220, 222, 224, and 226 may also have a length that is substantially equal to the length of the bandage 210 so that, in some embodiments, the tension indicators 216, 218, 220, 222, 224, and 226 collectively cover the bandage 210.

Each tension indicator 216, 218, 220, 222, 224, and 226 may be configured to color shift in response to a different pre-determined level of tension. In some embodiments, the tension indicators 216, 218, 220, 222, 224, and 226 respond to an increasing level of tension. For example, the tension indicator 216 may respond to the lowest level of tension, and the tension indicator 226 may respond to the highest level of tension. The tension indicators 218, 220, 222, and 224 may incrementally respond to increasing levels of tension between the lowest level of tension and the highest level of tension.

In some embodiments, the tension indicator 226 may color shift if a maximum level of tension is applied to the compression therapy apparatus 200. Each tension indicator 216, 218, 220, 222, and 224 may color shift in response to an incrementally lower level of tension. The incrementally lower levels of tension may be selected to indicate the relationship between the tension applied to the compression therapy apparatus 200 and the maximum level of tension. If tension is applied, as shown by the arrows in FIG. 4 and FIG. 5, the tension indicators 216, 218, 220, 222, 224, and 226 may each color shift in response to a different level of pre-determined tension. For example, in the illustrative embodiment of FIG. 4, the tension indicators 216, 218, and 220 have color shifted, as indicated by the shading of the tension indicators 216, 218, and 220. In the illustrative embodiment of FIG. 4, the tension applied to the compression therapy apparatus 200 may be about 50% of the maximum tension. In the illustrative embodiment of FIG. 5, the tension indicators 216, 218, 220, 222, and 224 have color shifted, as indicated by the shading of the tension indicators 216, 218, 220, 222, and 224. In the illustrative embodiment of FIG. 5, the tension applied to the compression therapy apparatus 200 may be about 83% of the maximum tension. In this manner, the tension indicators 216, 218, 220, 224, and 226 may provide an indication of how much tension has been applied to the compression therapy apparatus 200.

In some embodiments, a compression profile may be prescribed based on the maximum level of tension that may be indicated by the compression therapy apparatus 200. For example, if the tension indicator 226 color shifts at the maximum tension, a prescribed compression profile may be provided as 50% of the maximum tension. If the compression therapy apparatus 200 is applied to a limb, tension may be applied to the compression therapy apparatus 200 so that the tension indicators 216, 218, and 220 color shift, indicating that 50% of the maximum tension is being applied to the compression therapy apparatus 200. As used herein, the maximum tension refers to the maximum tension that may be indicated by the tension indicators 216, 218, 220, 222, 224, and 226.

Figure 6:
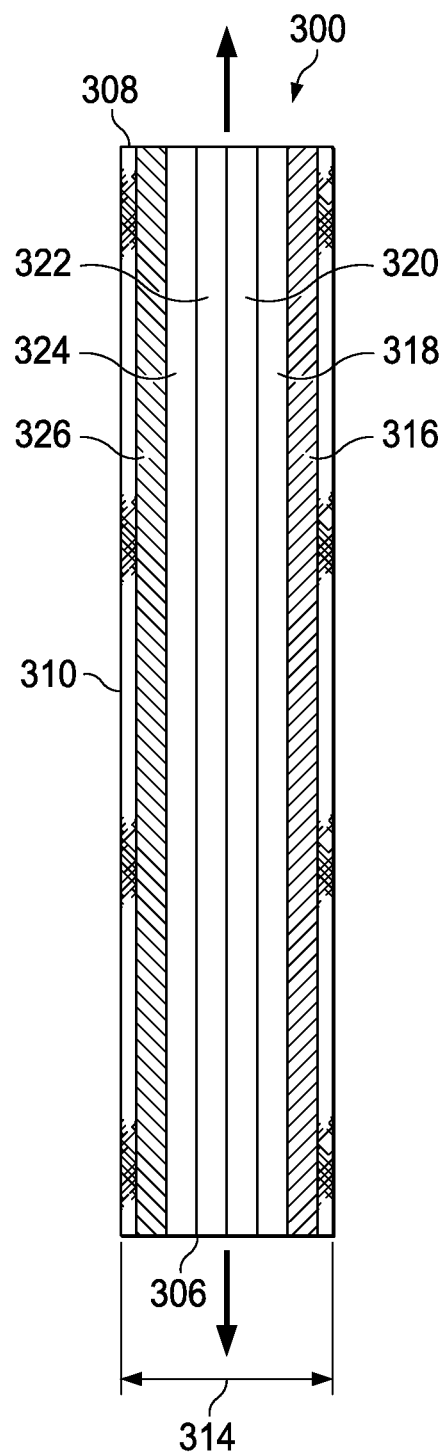
FIG. 6 is a plan view of another bandage in accordance with another embodiment.

FIG. 6 is a plan view, illustrating details that may be associated with another example embodiment of a compression therapy apparatus 300. The compression therapy apparatus 300 may be similar to and include the components of the compression therapy apparatus 100, modified as described in more detail below. Similar elements may include similar reference numbers indexed by 200. The compression therapy apparatus 300 may include a bandage 310 and tension indicators 316, 318, 320, 322, 324, and 326. Each tension indicator 316, 318, 320, 322, 324, and 326 may be similar to and operate in a manner similar to the tension indicator 102 described above.

The tension indicators 316, 318, 320, 322, 324, and 326 may be disposed on the bandage 310 so that the tension indicators 316, 318, 320, 322, 324, and 326 are distributed across a width 314 of the bandage 310. As shown in FIG. 6, for example, the tension indicators 316, 318, 320, 322, 324, and 326 may be equally apportioned across the width 314, so that the width of each of the tension indicators 316, 318, 320, 322, 324, and 326 is substantially equal. In some embodiments, the tension indicators 316, 318, 320, 322, 324, and 326 may also be disposed in parallel on the bandage 310. Any or all of the tension indicators 316, 318, 320, 322, 324, and 326 may also have a length that is substantially equal to the length of the bandage 310 so that, in some embodiments, the tension indicators 316, 318, 320, 322, 324, and 326 collectively cover the bandage 310.

Each tension indicator 316, 318, 320, 322, 324, and 326 may be configured to color shift in response to the same pre-determined level of tension. The tension indicators 316, 318, 320, 322, 324, and 326 may be disposed across the width 314 of the bandage 310 so that each tension indicator 316, 318, 320, 324 and 326 may indicate the level of tension for a portion of the width 314 of the compression therapy apparatus 300. If tension is applied to only a portion of the width 314 of the compression therapy apparatus 300, only the tension indicator 316, 318, 320, 324, or 326 proximate to the application of tension may experience the color shift. In this manner, the tension indicators 316, 318, 320, 324, and 326 may indicate if tension is unevenly applied across the width 314 of the compression therapy apparatus 300. For example, as shown by the arrows in FIG. 6, the tension may be applied proximate to the edges but not at the middle portion of the compression therapy apparatus 300. In response, the tension indicators 316 and 326 may experience the color shift, indicating that tension may not be applied to the middle portion of the compression therapy apparatus 300.

Figure 7:
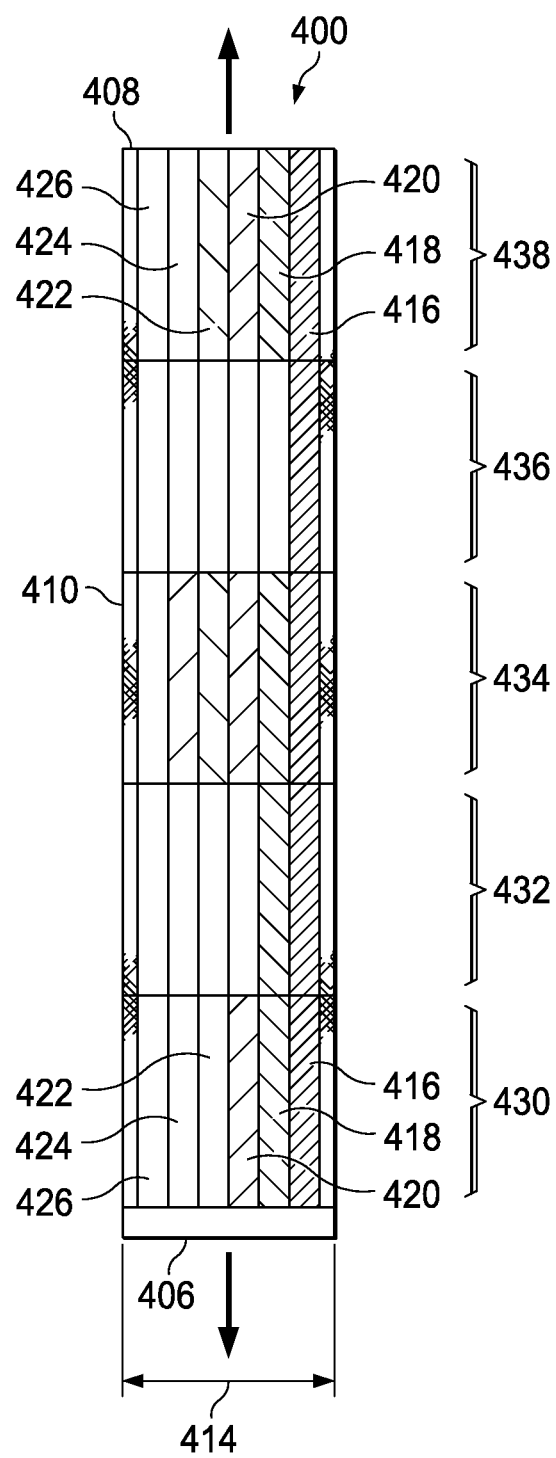
FIG. 7 is a plan view of another bandage in accordance with another embodiment.

FIG. 7 is a plan view, illustrating details that may be associated with another example embodiment of a compression therapy apparatus 400. The compression therapy apparatus 400 may be similar to and include the components of the compression therapy apparatus 100, modified as described in more detail below. Similar elements may include similar reference numbers indexed by 300, for example, the compression therapy apparatus 400 may include a bandage 410.

In some embodiments, the compression therapy apparatus 400 may be divided into compression zones. The compression zones may be equally apportioned along a length of the compression therapy apparatus 400 in some embodiments. For example, a first compression zone 430, a second compression zone 432, a third compression zone 434, a fourth compression zone 436, and a fifth compression zone 438 may be equally apportioned along a length of the compression therapy apparatus 400, as shown in FIG. 7. The compression zones may also be linked together in a series, so that each compression zone is concatenated with at least one adjacent compression zone. For example, the first compression zone 430 may be proximate to the first end 406 and the fifth compression zone 438 may be proximate to the second end 408. The second compression zone 432, the third compression zone 434, and the fourth compression zone 436 may be sequentially distributed along the length of the compression therapy apparatus 400 between the first compression zone 430 and the fifth compression zone 438.

In some embodiments, each compression zone 430, 432, 434, 436, and 438 may include more than one tension indicator. For example, each compression zone 430, 432, 434, 436, and 438 includes six tension indicators 416, 418, 420, 422, 424, and 426. Each tension indicator 416, 418, 420, 422, 424, and 426 may be similar to and operate in a manner similar to the tension indicator 102 described above.

The tension indicators 416, 418, 420, 422, 424, and 426 may be disposed on the bandage 410 so that the tension indicators 416, 418, 420, 422, 424, and 426 may be distributed across a width 414 of each compression zone 430, 432, 434, 436, and 438. As shown in FIG. 7, for example, the tension indicators 416, 418, 420, 422, 424, and 426 may be apportioned across the width 414. In more particular embodiments, the tension indicators 416, 418, 420, 422, 424, and 426 may be apportioned equally, so that the width of the tension indicators 416, 418, 420, 422, 424, and 426 is substantially equal. In some embodiments, the tension indicators 416, 418, 420, 422, 424, and 426 may also be disposed in parallel across each compression zone 430, 432, 434, 436, and 438.

Each tension indicator 416, 418, 420, 422, 424, and 426 may be configured to color shift in response to a different pre-determined level of tension. In some embodiments, the tension indicators 416, 418, 420, 422, 424, and 426 may respond to an increasing level of tension with the tension indicator 416 responding to the lowest level of tension, the tension indicator 426 responding to the highest level of tension, and the tension indicators 418, 420, 422, and 424 responding to incremental levels of tension between the lowest level of tension and the highest level of tension. The tension indicators 416, 418, 420, 422, 424, and 426 have a length less than the length of the compression therapy apparatus 400 so that each tension indicator 416, 418, 420, 422, 424, and 426 may only provide an indication of the tension applied to the compression zone 430, 432, 434, 436, and 438 in which the tension indicators 416, 418, 420, 422, 424, and 426 may be located.

If tension is applied, as shown by the arrows in FIG. 7, the tension indicators 416, 418, 420, 422, 424, and 426 may each color shift if their particular level of pre-determined tension is reached in their particular compression zone 430, 432, 434, 436, and 438. For example, in the first compression zone 430, the tension indicators 416, 418, and 420 have color shifted. Consequently, the compression therapy apparatus 400 has approximately 50% of the maximum tension applied to the compression therapy apparatus 400 in the first compression zone 430. In the second compression zone 432, the tension indicators 416 and 418 have color shifted. Consequently, the compression therapy apparatus 400 has approximately 33% of the maximum tension applied to the compression therapy apparatus 400 in the second compression zone 432. In the third compression zone 434, the tension indicators 416, 418, 420, 422 and 424 have color shifted. Consequently, the compression therapy apparatus 400 has approximately 83% of the maximum tension applied to the compression therapy apparatus 400 in the third compression zone 434. In the fourth compression zone 436, the tension indicator 416 has color shifted. Consequently, the compression therapy apparatus 400 has approximately 16% of the maximum tension applied to the compression therapy apparatus 400 in the fourth compression zone 436. In the fifth compression zone 438, the tension indicators 416, 418, 420, and 422 have color shifted. Consequently, the compression therapy apparatus 400 has approximately 65% of the maximum tension applied to the compression therapy apparatus 400 in the fifth compression zone 438. As used herein, the maximum tension refers to the maximum tension that may be indicated by the tension indicators 416, 418, 420, 422, 424, and 426.

The compression zones 430, 432, 434, 436, and 438 may allow a compression profile of the compression therapy apparatus 400 to be more specifically tailored to a particular limb being treated. For example, a clinician may determine that different portions of a limb may need different levels of compression that may not be satisfied by a standard compression profile provided by a constant level of tension and an increasing circumference of the limb. As each tension indicator 416, 418, 420, 422, 424, and 426 of each compression zone 430, 432, 434, 436, and 438 may indicate a different level of tension, a clinician may prescribe a specific amount of tension for each portion of a limb covered by a different compression zone 430, 432, 434, 436, and 438. As the level of tension causing each tension indicator 416, 418, 420, 422, 424, and 426 may be known, a clinician may prescribe a first level of tension for the first compression zone 430, a second level of tension for the second compression zone 432, and so on. Each level of tension may correspond with a different tension indicator 416, 418, 420, 422, 424, and 426 so that if the appropriate tension indicator 416, 418, 420, 422, 424, and 426 color shifts, a clinician may know that a desired compression for that portion of a limb has been achieved. For example, in FIG. 7, the compression prescribed for the first compression zone 430 may correspond with a tension level that may be indicated by the tension indicator 420. Consequently, a clinician may apply tension to the compression therapy apparatus 400 while wrapping the compression therapy apparatus 400 around a limb so that the tension indicators 416, 418, and 420 have color shifted. Once the portion of the compression therapy apparatus 400 that corresponds with the first compression zone 430 has been wrapped around a limb, a clinician may apply a different level of tension to the compression therapy apparatus 400 while wrapping a portion of the compression therapy apparatus 400 that corresponds with the second compression zone 432 around the limb. In some embodiments, the compression prescribed for the second compression zone 432 may correspond with a tension level that may be indicated by the tension indicator 418. A clinician may apply tension to the compression therapy apparatus 400 while wrapping the compression therapy apparatus 400 around a limb so that the tension indicators 416 and 418 color shift. Once a portion of the compression therapy apparatus 400 that corresponds with the second compression zone 432 has been wrapped around a limb, a clinician may apply a different level of tension to the compression therapy apparatus 400 while wrapping a portion of the compression therapy apparatus 400 that corresponds with the third compression zone 434, the fourth compression zone 436, and the fifth compression zone 438 around the limb.

The systems and methods described herein may provide significant advantages, some of which have already been mentioned. For example, the compression therapy apparatus 100 may provide clinicians with a more objective indication of a level of tension applied to the compression therapy apparatus 100 without relying on the subjective judgment of the clinician. The indication may be provided solely by the presence or absence of color so that users who may be colorblind may not be hindered by use of the compression therapy apparatus 100. In addition, the compression therapy apparatus 100 may provide a clinician with the ability to determine whether tension is being applied to the compression therapy apparatus 100 uniformly. The compression therapy apparatus 100 may also be able to indicate the particular areas in which varying levels of tension are being applied.

Although certain illustrative, non-limiting embodiments have been presented, it should be understood that various changes, substitutions, permutations, and alterations can be made without departing from the scope the appended claims. It will be appreciated that any feature that is described in connection to any one embodiment may also be applicable to any other embodiment.

It will be understood that the benefits and advantages described above may relate to one embodiment or may relate to several embodiments. It will further be understood that reference to "an" item refers to one or more of those items.

The steps of the methods described herein may be carried out in any suitable order, or simultaneously where appropriate.

Where appropriate, features of any of the embodiments described above may be combined with features of any of the other embodiments described to form further examples having comparable or different properties and addressing the same or different problems.

It will be understood that the above description of preferred embodiments is given by way of example only and that various modifications may be made by those skilled in the art. The above specification, examples, and data provide a complete description of the structure and use of exemplary embodiments. Although various embodiments have been described above with a certain degree of particularity, or with reference to one or more individual embodiments, those skilled in the art could make numerous alterations to the disclosed embodiments without departing from the scope of the claims.

What is claimed is:

1. A compression therapy apparatus, comprising:
   a bandage; and
   a tension indicator comprising layers of liquid crystal droplets deposited on a polymer matrix, the tension indicator coupled to the bandage and adapted to color shift under tension.

2. The compression therapy apparatus of claim 1, wherein the bandage and the tension indicator have equal lengths.

3. The compression therapy apparatus of claim 1, wherein the bandage and the tension indicator have equal widths.

4. The compression therapy apparatus of claim 1, wherein the tension indicator comprises a plurality of tension indicators coupled to the bandage across a width of the bandage.

5. The compression therapy apparatus of claim 1, wherein the tension indicator comprises a plurality of tension indicators coupled to the bandage across a width of the bandage, each tension indicator adapted to indicate tension in a portion of the width of the bandage.

6. The compression therapy apparatus of claim 1, wherein the tension indicator comprises a plurality of tension indicators coupled to the bandage across a width of the bandage, each tension indicator adapted to indicate a different predetermined tension.

7. The compression therapy apparatus of claim 1, wherein the tension indicator comprises a plurality of tension indicators, each tension indicator coupled to the bandage along a length of the bandage.

8. The compression therapy apparatus of claim 1, wherein the tension indicator comprises a plurality of tension indicators, each tension indicator coupled to the bandage along a length of the bandage and adapted to indicate tension in a portion of the length of the bandage.

9. The compression therapy apparatus of claim 1, wherein:
the tension indicator comprises a plurality of tension indicators, each tension indicator coupled to the bandage along a length of the bandage and adapted to indicate tension in a portion of the length of the bandage; and
each tension indicator is disposed linearly along the length of the bandage.

10. The compression therapy apparatus of claim 1, wherein:
the tension indicator comprises a plurality of tension indicators, each tension indicator coupled to the bandage along a length of the bandage and adapted to indicate tension in a portion of the length of the bandage; and
each tension indicator is disposed linearly along the length of the bandage so that an end of a first tension indicator is adjacent to an end of a second tension indicator.

11. The compression therapy apparatus of claim 1, wherein:
the tension indicator comprises a plurality of tension indicators, each tension indicator coupled to the bandage along a length of the bandage and adapted to indicate tension in a portion of the length of the bandage;
each tension indicator is disposed linearly along the length of the bandage so that an end of a first tension indicator is adjacent to an end of a second tension indicator; and
the tension indicators are coupled to the bandage across a width of the bandage.

12. The compression therapy apparatus of claim 1, wherein:
the tension indicator comprises a plurality of tension indicators, each tension indicator coupled to the bandage along a length of the bandage and adapted to indicate tension in a portion of the length of the bandage;
each tension indicator is disposed linearly along the length of the bandage so that an end of a first tension indicator is adjacent to an end of a second tension indicator;
the tension indicators are coupled to the bandage across a width of the bandage; and
each tension indicator is adapted to indicate tension in a portion of the width of the bandage.

13. The compression therapy apparatus of claim 1, wherein:
the tension indicator comprises a plurality of tension indicators, each tension indicator coupled to the bandage along a length of the bandage and adapted to indicate tension in a portion of the length of the bandage;
each tension indicator is disposed linearly along the length of the bandage so that an end of a first tension indicator is adjacent to an end of a second tension indicator;
the tension indicators are coupled to the bandage across a width of the bandage; and
each tension indicator is adapted to indicate a different predetermined tension.

14. The compression therapy apparatus of claim 1, further comprising one or more couplers adapted to couple at least one of the first end and the second end to a portion of the bandage.

15. The compression therapy apparatus of claim 1, wherein the tension indicator comprises a holographically formed polymer dispersed liquid crystal film.

16. The compression therapy apparatus of claim 1, wherein the color shift comprises changing from a first color to a second color when tension is applied to the bandage.

17. The compression therapy apparatus of claim 1, wherein the color shift comprises the tension indicator changing from a milky color to a blue color.

18. The compression therapy apparatus of claim 1, wherein the tension indicator is woven into the bandage.

19. The compression therapy apparatus of claim 1, wherein the polymer matrix is an elastic polymer matrix.

20. The compression therapy apparatus of claim 1, wherein the bandage and the polymer matrix are configured to deform at substantially the same rate.

21. The compression therapy apparatus of claim 1, wherein the tension indicator comprises a plurality of tension indicators distributed across a width of the bandage.

22. The compression therapy apparatus of claim 1, wherein the tension indicator comprises a plurality of tension indicators apportioned across a width of the bandage.

23. The compression therapy apparatus of claim 1, wherein the tension indicator comprises a plurality of tension indicators equally apportioned across a width of the bandage.

24. The compression therapy apparatus of claim 1, wherein the tension indicator comprises a plurality of tension indicators distributed across a width of the bandage and in parallel along a length of the bandage.

25. A method of manufacturing a bandage comprising:
providing a bandage; and
coupling a tension indicator to the bandage, the tension indicator adapted to color shift under tension, the tension indicator comprising layers of liquid crystal droplets deposited on a polymer matrix.

26. The method of claim 25, wherein coupling the tension indicator comprises adhering the tension indicator to a surface of the bandage.

27. The method of claim 25, wherein coupling the tension indicator comprises weaving the tension indicator into the bandage.

28. The method of claim 25, wherein coupling the tension indicator comprises bonding the tension indicator to a surface of the bandage.

29. The method of claim 25, wherein the tension indicator comprises a plurality of tension indicators.

30. A method for providing compression therapy to a tissue site, the method comprising:
providing a compression therapy apparatus, comprising:
a bandage, and
a tension indicator comprising layers of liquid crystal droplets deposited on a polymer matrix, the tension indicator coupled to the bandage and adapted to color shift under tension;
securing the first end of the bandage to the tissue site;
applying tension to the bandage;
monitoring the tension indicator for the color shift; and
if the tension indicator color shifts, wrapping the bandage around the tissue site.

31. The method of claim 30, wherein the tension indicator comprises a plurality of tension indicators coupled to the bandage across a width of the bandage.

32. The method of claim 30, wherein the tension indicator comprises a plurality of tension indicators coupled to the bandage across a width of the bandage, each tension indicator adapted to indicate tension in a portion of the width of the bandage.

33. The method of claim 30, wherein the tension indicator comprises a plurality of tension indicators coupled to the bandage across a width of the bandage, each tension indicator adapted to indicate a different predetermined tension.

34. The method of claim 30, wherein the tension indicator comprises a plurality of tension indicators, each tension indicator coupled to the bandage along a length of the bandage.

35. The method of claim 30, wherein the tension indicator comprises a plurality of tension indicators, each tension indicator coupled to the bandage along a length of the bandage and adapted to indicate tension in a portion of the length of the bandage.

36. The method of claim 30, wherein:
the tension indicator comprises a plurality of tension indicators, each tension indicator coupled to the bandage along a length of the bandage and adapted to indicate tension in a portion of the length of the bandage; and
each tension indicator is disposed linearly along the length of the bandage.

37. The method of claim 30, wherein:
the tension indicator comprises a plurality of tension indicators, each tension indicator coupled to the bandage along a length of the bandage and adapted to indicate tension in a portion of the length of the bandage; and
each tension indicator is disposed linearly along the length of the bandage so that an end of a first tension indicator is adjacent to an end of a second tension indicator.

38. The method of claim 30, wherein:
the tension indicator comprises a plurality of tension indicators, each tension indicator coupled to the bandage along a length of the bandage and adapted to indicate tension in a portion of the length of the bandage;
each tension indicator is disposed linearly along the length of the bandage so that an end of a first tension indicator is adjacent to an end of a second tension indicator; and
the tension indicators are coupled to the bandage across a width of the bandage.

39. The method of claim 30, wherein:
the tension indicator comprises a plurality of tension indicators, each tension indicator coupled to the bandage along a length of the bandage and adapted to indicate tension in a portion of the length of the bandage;
each tension indicator is disposed linearly along the length of the bandage so that an end of a first tension indicator is adjacent to an end of a second tension indicator;
the tension indicators are coupled to the bandage across a width of the bandage; and
each tension indicator is adapted to indicate tension in a portion of the width of the bandage.

40. The method of claim 30, wherein:
the tension indicator comprises a plurality of tension indicators, each tension indicator coupled to the bandage along a length of the bandage and adapted to indicate tension in a portion of the length of the bandage;
each tension indicator is disposed linearly along the length of the bandage so that an end of a first tension indicator is adjacent to an end of a second tension indicator;
the tension indicators are coupled to the bandage across a width of the bandage; and
each tension indicator is adapted to indicate a different predetermined tension.

* * * * *